US006320033B1

(12) United States Patent
Bourbonnais et al.

(10) Patent No.: US 6,320,033 B1
(45) Date of Patent: Nov. 20, 2001

(54) CANDIDA ALBICANS GENE (CSA1) ENCODING A MYCELIAL SURFACE ANTIGEN, AND USES THEREOF

(75) Inventors: Yves Bourbonnais, Cap-Rouge; Noëlla Deslauriers, St-Ferréol-les-Neiges, both of (CA)

(73) Assignee: Université Laval, Québec (CA)

( * ) Notice: Subject to any disclaimer, the term of this patent is extended or adjusted under 35 U.S.C. 154(b) by 0 days.

(21) Appl. No.: 09/351,200

(22) Filed: Jul. 9, 1999

(30) Foreign Application Priority Data

Jul. 10, 1998 (CA) .................................................. 2237134

(51) Int. Cl.[7] .............................. C12Q 1/68; C07H 21/00
(52) U.S. Cl. .................... 536/23.1; 435/6; 435/254.22; 536/23.74; 536/24.32
(58) Field of Search ................................ 536/23.1, 24.32, 536/23.74; 435/254.22, 922, 6

(56) References Cited

PUBLICATIONS

Stratagene 1991 Produce Catalog, Cat. # 300387, p. 66.*
GenEMBL Accession No. AF080221, Canadida albicans mycelial surface antigen precursor (CSA1) gene. Made publicly available Aug. 09, 1998.*
GenEMBL Accession No. U57887, Thanatephorus cucumeris strain 021R06 5.8S ribosomal RNA gene. Made publicly available Mar. 30, 1997.*
GenEMBL Accession No. X78138, Human 14–3–3 eta subtype mRNA. Made publicly available Mar. 14, 1994.*
EST Accession No. T11718, Human heart cDNA of HS1 protein, mRNA sequence. Made publicly available Nov. 28, 1994.*
EST Accession No. R25364, Human placental 14–3–3 eta protein. Made publicly available Apr. 24, 1995.*
Deslauriers, N., et al., *Microbiology* 142: 1239–1248, 1996.
Dugger, K. O., et al., *Biochem. Biophys. Res. Commun.* 218: 485–489, 1996.
Fonzi, W. A., and Irwin, M. Y., *Genetics* 134:717–728, 1993.
Kaiser, C., et al., *Laboratory Course Manual for Methods in Yeast Genetics*. Cold Spring Harbor Laboratory, New York: Cold Spring Harbor Laboratory Press. 1994.
Kershaw, M. J., et al., *EMBO L*. 17: 3838–3849, 1998.
Kohrer, K., and Domdey, H., *Methods Enzymol.* 194: 398–405, 1991.
Ponton, J., et al., *Infect. Immun.*, 61: 4842–4847, 1993.
Pringle, J. R., et al., *Methods Enzymol.* 194: 565–602, 1991.
Staab, J. F., et al., *Science* 283: 1535–1538, 1999.
Thomas, B. J., and Rothstein, R., *Cell* 56: 619–630, 1989.

* cited by examiner

*Primary Examiner*—Ardin H. Marschel
(74) *Attorney, Agent, or Firm*—Nixon Peabody LLP

(57) ABSTRACT

The present invention relates to a *Candida albicans* gene (CSA1) encoding a surface protein. The present invention also relates to the surface protein and methods for using the protein or the gene for the detection, prophylaxis or treatment of candidal infection. The protein encoded is a surface antigen of *Candida albicans* yeast and mycelial forms, respectively. The mycelial surface antigen was shown to be present predominantly in the terminal third of the hyphal structures. CSA1 is a gene coding for a unique surface antigen.

2 Claims, 11 Drawing Sheets

```
MLPSIVISIVLASFVSAESSITEAPTTTAEDNPYTIYPSVAKTASINGFADRIYDQLPEC   60

AKPCMFQNTGVTPCPYWDTGCLCIMPTFAGAIGSCIAEKCKGQDVVSATSLGTSICSVAG  120

VWDPYWMVPANVQSSLSAAATAVASSSEQPVETSSEPAGSSQSVESSQPAETSSSEPAET  180

SSSEPAETSSETSSEQPASSEPAETSSEESSTITSAPSTPEDNPYTIYPSVAKTASINGF  240

ADRIYDQLPECAKPCMFQNTGVTPCPYWDTGCLCIMPTFAGAIGSCIAEKCKGQDVVAAT  300

SLGTSICSVAGVWDPYWMVPANVQSSLSAAATAVPSSSEQSVETSSESAESSQSVESSQP  360

AETSSEQPSETSSETSSQQLSSITSAPDSSATSSSSTTSTFIRTASINGFADKLYDQLPE  420

CAKPCMFQNTGITPCPYWDAGCLCVMPQFAGAIGSCVADSCKGQDIVSVTSLGTSVCSVA  480

GVNAPYWMLPASVKSSLSVAATAVPTSDSASETASQEPSETSSEQPSETASQQPAETSSE  540

ESSTITSAPSTPEDNPYTIYPSVAKTASINGFADRIYDQLPECAKPCMFQNTGVTPCPYW  600

DTGCLCIMPTFAGAIGSCIAEKCKGQDVVSATSLGTSICSVAGVWDPYWMIPANAQSSLN  660

AAATAVASSSEQPVETSSEAAESSQNPAESSSQQPSETASQEPSETSSQEPSESSSEQPA  720

ETSSEESSTITSAPSTPEDNPYTIYPSVAKTASINGFADRIYDQLPECAKPCMFQNTGVT  780

PCPYWDTGCLCIMPTFAGAIGSCIAEKCKGQEVVSVTSLGSSICSVAGVWDPYWMLPANV  840

QSSLNAAATAVATSDSASEVASASESASQVPQETSAASSQSANNSVASAAPSNSSVSAAP  900
                                        *               *
SSNSSGVPAAPSNNSSGASVVPSQSANNSSASAAPSNNSSSAISGSVAPSSYGNSTIAQP  960
         *    **          **        **                *
STSTKSDAASITGPITTDKVITNESGIVFTSTVIITHVSEYCDQTSAAAVQSSACEEQSS 1020

AKSEQASASSEQVKVITSVVWCESSIQSIESVKTSAEAAHKTEVIASCASELSSLSSAKS 1080

EAMKTVSSLVEVQKSAVAKQTSLAAVQSSAASVQLSAAHAQKSSEAVEVAQTAVAEASKA 1140

GDEISTEIVNITKTVSSGKETGVSQATVAANTHSVAIANMANTKFASTMSLLVASFVFVG 1200

LFI                                                          1203
```

```
Csa1p (417-445) : QLPE---CA..CMFQNTG.T.-C.-..DA----.CLCV-
Ag2   (19-51)   : QLPD...CAL.CFVE..G...-CT.L.D.----.C.C.-
Pth11p (34-67)  : ..P.---CAM.C-F.DA..S..CS-L..A.....CICV.

Csa1p (446-482) : .PQFAGAI.SCV.DSCK-.QEIVSVT.L..SVCS.AGV
Ag2   (52-88)   : .PEL.G.IT.CVEEAC.-.D..ISVS.IVV..CS.AGV
Pth11p (68-104) : .P.LS-T.ATCVQ.SCK..EQLVA....LFSLC....M
```

FIG. 3

ATCC 32354

CA14

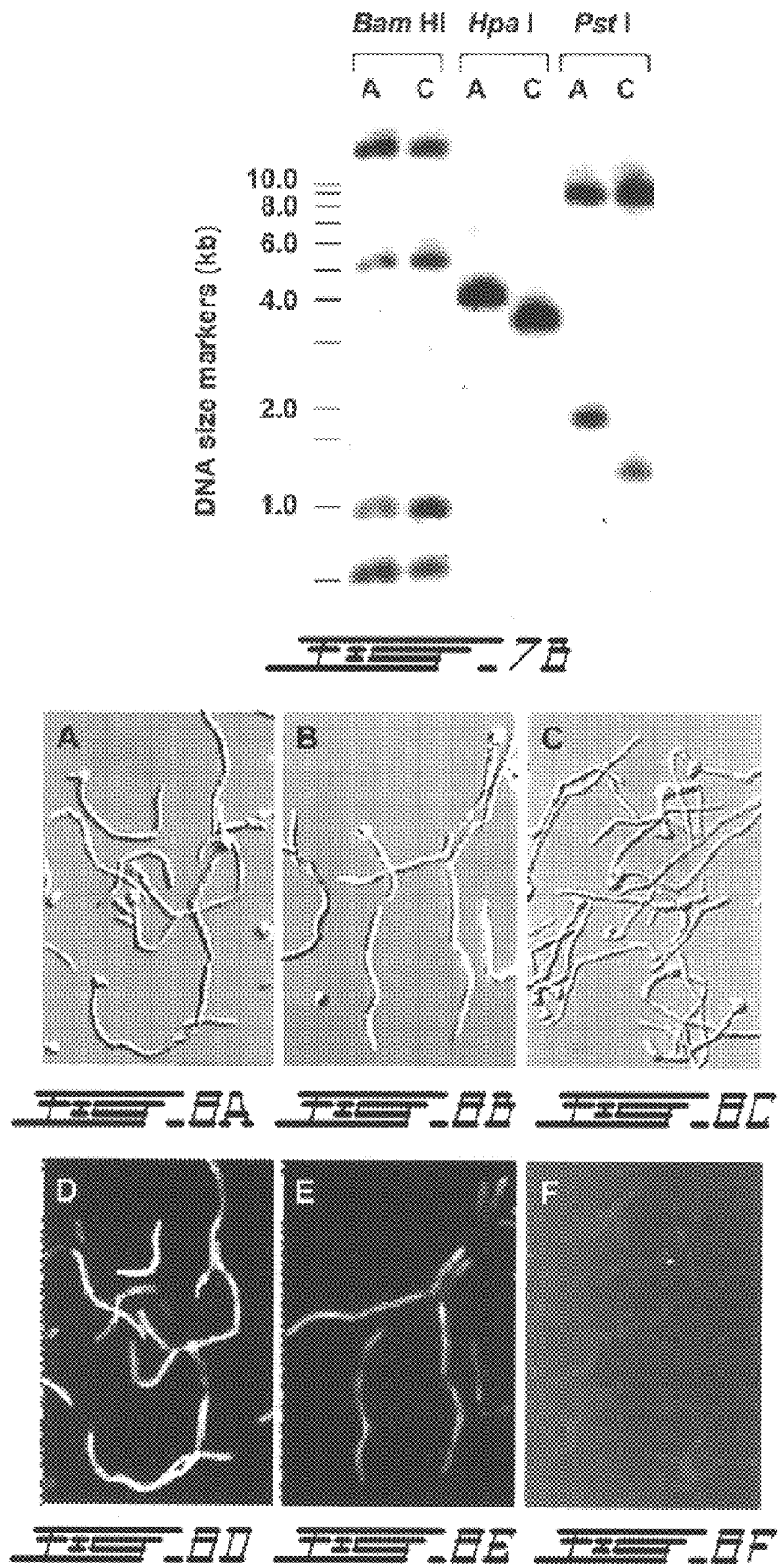

CANDIDA ALBICANS GENE (CSA1) ENCODING A MYCELIAL SURFACE ANTIGEN, AND USES THEREOF

BACKGROUND OF THE INVENTION (a) Field of the Invention

The invention relates to *Candida albicans* gene (CSA1) encoding a mycelial surface antigen, and uses thereof for the treatment or prophylaxis of candidal infections.

(b) Description of Prior Art

*Candida albicans* is of major medical importance, being the most commonly isolated fungal species from various mucosal surfaces in healthy individuals and from infectious sites in patients with candidiasis. Most frequently, it causes superficial, irritating infections of the oral and urogenital tracts. However, serious deep-seated or systemic infections can develop, particularly in immunocompromised subjects.

The performance of *Candida albicans* as an opportunistic pathogen is associated with a number of factors that include the morphological and functional modifications resulting from switching between the yeast and the hyphal forms. Mycelium formation is believed to contribute to fungal adhesion to host cell surfaces and to facilitate invasion of a variety of host tissues through the expression of specialized surface proteins and enzymes (Staab, J. F., et al., *Science* 283: 1535–1538, 1999). On the basis that the dimorphic process is likely to be associated with differential expression of mycelial cell-specific molecules, biochemical and immunological approaches have been used for their identification.

The success of immunological approaches largely depends on the nature and specificity of the antibody preparation but recently the use of monoclonal antibodies (MAbs) has proven invaluable in the screening of yeast versus mycelial antigens. As summarized by Ponton et al., (Ponton, J., et al., *Infect. Immun.*, 61: 4842–4847, 1993), different types of germ tube surface antigens have been described but true hyphal antigens (type I antigens) appear to be scarce because most hyphae-specific MAbs also react with either DTT-treated (stripped) yeast cells (type II antigens) or both yeast cells and germ tubes (type IV antigens).

It would be highly desirable to be provided with a *Candida albicans* surface antigen for the detection, treatment or prophylaxis of candidal infections.

SUMMARY OF THE INVENTION

One aim of the present invention is to provide a nucleic acid sequence encoding a *Candida albicans* surface antigen for the detection, treatment or prophylaxis of candidal infections.

Another aim of the present invention is to provide a detection kit for candidal infection.

In accordance with the present invention there is provided a nucleic acid sequence as follows:

```
gtcgacacaa taagctaaat agagtgcagt aagatgtgat tgtcatcttt agtagatgct  (SEQ ID NO:1)

cctataggta attgtataa9 gttattgcgg agttaacgct ggtattgggt ttcgcttggt agtttctagt attggcacta aaattttttt tttcttgttt gtcgcacaca cagttgattg gctagaatta aagctcaact ttgcacaatt taaaaacaat gcattaggcg atttatcgcg taaattaatt accacaacaa agaacaactt attttccgat tgtccaatca atgtcatagg tgttctcggg tttgttacaa tgtctggaaa tatcgaaaac ttacgataat ttaaatgttg gtttgtggat tttagaaggg ataatacaat gattggatag cactaagtcc cgtatagttc gacaacggtt tatttgggtt actacttata gagccctggt ccccagaatt tgaaaatgta gttggttgtg aaacactcag ggatatactc aacaatgctt ccatccatty ttatttcaat cgttttagca tcctttgtga gtgcagaatc atctattaca gaagcaccaa caacaaccgc tgaagataat ccatatacta tctacccaag tgttgccaag actgcttcta tcaatggttt tgctgacaqa atttatgatc aattgccaga gtgtgccaag ccatgtatgt tccaaaacac tggtgtgacc ccatgtccat actgggatac tgggtgtttg tgtattatgc caacatttgc tggtgccatt ggttcttgta ttgctgagaa gtgtaaaggc caagacgttg tttctgctac aagtttggga acttccattt gttccgttgc tggtgtgtgg gatccatact ggatgqtqcc tgcaaatgtc cagagcagtt taagtgctgc tgccactgct gttgcatcgt cttctgaaca accagttgaa acatcttctg aaccagctgg atcttctcag tctgttgaat cttctcaacc tgctgaaacc tcatcatctg aacctgctga gacttcatca tctgaacctg ctgagacttc atcggaaaca tcatccgaac aacctgcttc atctgaacct gctgaaactt catcagaaga atcttctaca atcacttcag ccccatcaac tcctgaagat aacccataca ccatctaccc aagtgttgcc aagactgctt ctatcaatgg ttttgctgac agaatctacg accaattgcc
```

-continued

```
agagtgtgcc aagccatgta tgttccaaaa cactggtgtg accccatgtc catactggga tactgggtgc ttgtgtatta tgccaacatt tgctggtgcc attgggtctt gtattgctga gaagtgtaaa ggccaagacg ttgttgctgc tacaagtttg gqaacttcca tttgttccgt tgctggtgtq tgggatccat actggatggt qcotgcaaat gtccagagca gtttaagtgc tgctgccact gctgttccat catcctccga acaatcagtt gaaacatctt ctgaatcagc tgaatcttct cagtctgttg aatcttctca acctgctgaa acctcatctg aacaaccatc tgagacttca tctgaaactt cttcccaaca actttcaagt atcacttcag caccagactc ctccgctaca agcagctcct caaccacatc tacttttatt agaactgctt ccattaatgg ttttgctgat aaactttacg accaattacc agaatgtgct aaaccatgta tgttccaaaa tactggcata acaccatgtc catactggga tgccggttgt ttatgtgtca tgccacaatt tgcaggtgct attggttcat gtgttgccga tagttgtaaa ggtcaagata ttgtttctgt caccagcttg ggtacttctg tttgttctgt tgccggtgtt aatgcacctt attggatgct tccagctagt gttaaaagta gcttaagtgt tgctgctact gcagtaccaa cctccgacag tgcatctgaa actgcttccc aagaaccatc tgaaacttca tctgaacagc catcagaaac tgcttcacaa caacctgctg aaacttcatc agaagaatct tctacaatca cttoagcccc atcaactcct gaagataacc catacaccat ctacccaagt gttgccaaga ctgcttctat caatggtttt gctgacagaa tctacgacca attgccagag tgtgccaagc catgtatgtt ccaaaacact ggtgtgaccc catgtccata ctgggatact gggtgcttgt gtattatgcc aacatttgct ggtgccattg ggtcttgtat tgctgagaag tgtaaaggcc aagacgttgt ttctgctaca agtttgggaa cttccatttg ttccgtcgct ggtgtatggg atccatattg gatgattcca gctaatgcac aaagcagttt gaatgctgct gccactgctg ttgcatcatc ttctgaacaa ccagttgaaa catcttctga agctgctgaa tcttctcaaa atcctgctga atcttcttct caacaaccat ctgaaactgc ttctcaagaa ccatctgaaa cttcttccca agaaccatca gaaagctcat cagagcaacc tgctgagact tcatcagaag aatcttctac catcacttca gctccatcaa ctcctgaaga taatccatac accatctacc caagtgttgc caagactgct tctatcaatg gttttgctga cagaatttat gatcaattgc cagagtgtgc caagccatgt atgttccaaa acactggtgt gaccccatgt ccatactggg atactgggtg cttgtgtatt atgccaacat tgctggtgc cattgggtct tgtattgctg agaaatgtaa aggacaagag gttgtttctg ttaca>tt gggtagctct atttgttccg ttgctggtgt atgggatcca tactggatgc ttccagctaa cgtgcaaagc agtttgaatg ccgctgccac tgctgttgca acttctgata gtgcatctga ggttgcttct gcttccgaat ccgcatctca agttccacaa gaaacttctg ctgcttcatc acaatcagcc aacaactcag ttgcttctgc tgctccatct aactcgtctg bttcagctgc tccatctagc aactcatctg gtgttccagc tgcgccatct aacaattcat ctggtgcttc agttgttcca tcacaatcag ccaacaattc atctgcttca gctgctccat ctaacaactc atctagtgct atttctggaa gtgttgcacc atcaagctac ggaaactcta ccattgcaca accatctact tctacaaaat ccgatgctgc atcaattact ggtccaatta ctacagacaa ggttataacc aatgagtctg gcattgtctt tacatctaca gtaatcatta cacatgtttc tgaatattgt gaccagactt ctgctgctgc tgttcaatca tcagcatgtg aagaacagtc aagtgctaaa tcagaacaag cttctgcttc atcagaacaa gttaaggtca ttactagtgt ggtttggtgt gagtcatcta ttcaatctat
```

-continued

```
tgaatctgtc aaaacaagtg cagaagctgc tcataagact gaggttattg ctagttgtgc aagtgaatta agctctttga gttctgctaa atctgaagct atgaagactg tttctagttt agttgaagtt caaaaatctq cagttgccaa acaaacctcg ttggctgctg tacaatcatc tgctgcttct gtacaattaa gtgctgctca cgcccaaaag tcgtctgagg cagttgaagt tgcccaaact gctgttgctg aagcttctaa agctggtgat gaaatttcga ctgaaattgt taacatcacc aagacagttt cttctggtaa ggagactggt gtttcccaag ctactgttgc tgctaacaca cattcagttg ctattgctaa tatggcaaat accaagtttg ccagcacaat gtcgttgttg gtcgctagtt tcgtgtttgt tggtctcttt atttaagagg tataataagt tcttataatt ttcttgataa atttatttt tttctgtttt cggttactat atgtataaag ttttgttaat actataattt ttttgttagc ctcggtattt cttaaaatag ttgtaaattc acccaaatag gaagacagaa aaaagtctag a       (4291 pb).
```

Also in accordance with the present invention, there is provided a probe derived from the above nucleic acid sequence. The probe is hybridizable with a sample of nucleic acid sequence of a patient for detecting CSA1 gene or its corresponding mRNA, the CSA1 gene or its corresponding mRNA when detected in the sample is indicative of the patient being infected with *Candida albicans*.

In accordance with the present invention, there is also provided a primer pair derived from the above nucleic acid sequence for amplifying the CSA1 gene or its corresponding mRNA.

Still in accordance with the present invention, there is provided a protein encoded by the above nucleic acid sequence. The protein preferably has a sequence as follows:

```
mlpsivisiv laefvsaess iteapttae  dnpytlypsv aktasingfa driydqlpec     (SEQ ID NO:2)

akpcmfqntg vtpcpywdtg clcimptfag aigsciaekc kgqdvvsats lgtsicsvag vwdpywmvpa nvqsslsaaa tavasssegp vetssepags sqsvessqpa etsssepaet sssepaetss etsseqpaee epaetseees stitsapstp ednpytiypa vaktasingf adriydqlpe cakpcmfqnt gvtpcpywdt gclcimptfa gaigsciaek ckgqdvvaat slgtsicsva gvwdpywmyp anvqsslsaa atavpssseq svetssesae ssqsvessqp aetsseqpse tssetssqql ssitsapdss atsssstttst firtasingf adklydqlpe cakpcmfqnt gitpcpywda gclcvmpqfa gaigscvads ckgqdivsvt slgtsvcsva gvnapywmlp asvksslsva atavptsdsa setasqepse tsseqpseta sqqpaetsse esstitsaps tpednpytiy psvaktasin gfadriydql pecakpcmfq ntgvtpcpyw dtgclcimpt fagaigscia ekckgqdvvs atslgtsics vagvwdpywm ipanaqssln aaatavasss eqpvetssea aessqnpaes ssqqp6etas qep6etssqe psessseqpa etsseessti tsapstpedn pytiypsvak tasingfadr iydqlpecak pcmfqntgvt pcpywdtgcl cimptfagai gsciaekckg qevvsvtslg ssicsvagvw dpywmlpanv qsslnaaata vatsdsasev asasesasqv pqetsaassq sannsvasaa psnssvsaap ssnssgvpaa psnnssgasv vpsqsannss asaapsnnss saisgsvaps sygnstiaqp stsktksdaas itgpittdkv itnesgivft stviithvse ycdqtsaaav qssaceeqss
```

-continued

```
akseqasass eqvkvitsvv wcessiqsie svktsaeaah kteviascas elsslssaks eamktvsslv evqksavakq tslaavqssa asvqlsaaha qksseaveva qtavaeaska gdeisteivn itktvssgke tgvsqatvaa nthsvaianm antkfastme llvasfvfvg lfi  (1203 aa).
```

The protein is more preferably a surface antigen of *Candida albicans*.

Further in accordance with the present invention, there is provided a vaccine against *Candida albicans*. The vaccine comprises the protein as described above, or an immunizing fragments thereof, in combination with a pharmaceutically acceptable excipient.

In accordance with the present invention, there is further provided a diagnostic kit for detecting *Candida albicans* infection in a sample of nucleic acid sequence of a patient. The kit comprises the nucleic acid sequence as defined above, or a fragment thereof capable of hybridizing with CSA1 gene of *Candida albicans*, or its corresponding mRNA. In an alternate kit, the kit may comprises at least one of i) a probe derived from a nucleic acid sequence as defined above, the probe being hybridizable with a nucleic acid sequence sample of a patient for detecting CSA1 gene or its corresponding mRNA, the CSA1 gene or its corresponding mRNA when detected in the sample is indicative of the patient being infected with *Candida albicans*, and ii) a primer pair derived from a nucleic acid sequence as defined above for amplifying CSA1 gene or its corresponding mRNA.

In accordance with the present invention, there is further provided a method for the diagnostic of a *Candida albicans* infection in a sample of nucleic acid sequence of a patient. The method comprises the steps of:
  a) amplifying the sample of nucleic acid sequence by polymerase chain reaction with a pair of primer as defined above; and
  b) detecting a fragment amplified in step a), wherein detection of the fragment is indicative of the sample of nucleic acid sequence being infected with *Candida albicans*.

Still in accordance with the present invention, there is provided a method for immunizing a patient from *Candida albicans*. The method comprises the step of administering an immunizing amount of a protein as defined above, or an immunologic fragment thereof, to a patient for inducing production of IgG antibodies against the protein.

The present invention still provides a method for treating a *Candida albicans* infection. The method comprises the step of administering an immunizing amount of a protein as defined above, or an immunologic fragment thereof, to a patient, wherein the protein is a surface antigen of *Candida albicans* and wherein administration of such protein on a mucosal surface of a patient induces production of IgG antibodies against the surface antigen.

Also in accordance with the present invention, there is provided an antibody directed against a protein as defined above for treating a Candidal infection, wherein the antibody binds to the protein for masking same and thereby reducing virulence of the Candidal infection. The antibody may be a polyclonal or monoclonal antibody. Preferably, the antibody is MAb 4E1 monoclonal antibody.

Further in accordance with the present invention, there is provided a method for treating a Candidal infection of a patient. The method comprises the step of administering to the patient an antibody as defined above, wherein the antibody binds to the protein for masking same and thereby reducing virulence of the Candidal infection.

The present invention has many applications. *Candida albicans* is a fungal human pathogen that infects the mucosal tissues and can elicit systemic infections in human. The major commercial applications of the present invention therefore concern the diagnostic, the prevention and the treatment of candidal infections.

As for the diagnostic, in a preferred embodiment of the invention, the presence of *Candida albicans* at sites of infection could be easily detected by polymerase chain reaction (PCR) with oligonucleotide primers derived from SEQ ID NO:1. The *Candida albicans* CSA1 gene encodes an abundant mycelial surface antigen. Expression of CSA1, or part thereof, in either bacteria or yeast and purification of the corresponding polypeptides can therefore, in combination with monoclonal antibodies such as MAb 4E1 directed against the CSA1 protein, can be used in ELISA assays to detect the presence of anti-CSA1 in sera of infected individuals.

As for the prevention of Candidal infections, purified proteins or peptides derived from expression of CSA1 in bacteria or yeast could also be used to immunize individuals against candidal infections. The CSA1 gene itself could be used in genetic vaccination against *C. albicans* through single or repeated injections of an eukaryotic expression vector carrying SEQ ID NO:1. Passive immunization, either through topical or systemic applications of the monoclonal antibodies directed against the CSA1 protein is also a potential commercial application.

As now for the treatment of Candidal infections, vaginal infections occur in immuno-competent patients and result from an inappropriate response of the immunity system. It has been demonstrated that vaginal allergic responses against *C. albicans* can predispose to recurrent candidal infection. Since CSA1 protein is a surface antigen that is shown to stimulate the production of IgG antibodies, single or repeated administrations of the purified CSA1 protein on the mucosal surface of the vagina may modulate the immune response and is effective in the treatment of recurrent vaginitis associated to *C. albicans*.

BRIEF DESCRIPTION OF THE DRAWINGS

FIG. 2B illustrates the deduced amino acid sequence of CSA1 using the single letter code;

FIG. 3 illustrates an alignment of the Csa1p CH domain with peptide sequences derived form the *C. immitis* Ag2 and *M. grisea* Pth11 proteins;

FIG. 6B illustrates a southern analysis of the genomic DNA extracted from the *C. albicans* strains ATCC 32354 and CAI4;

FIG. 7B illustrates the disruption of the CSA1 gene from *C. albicans*; and

FIGS. 8A to 8F illustrate the indirect immunofluorescence microscopy of the *C. albicans* csa1Δ mutant strains with MAb 4E1.

DETAILED DESCRIPTION OF THE INVENTION

Figure 1A:
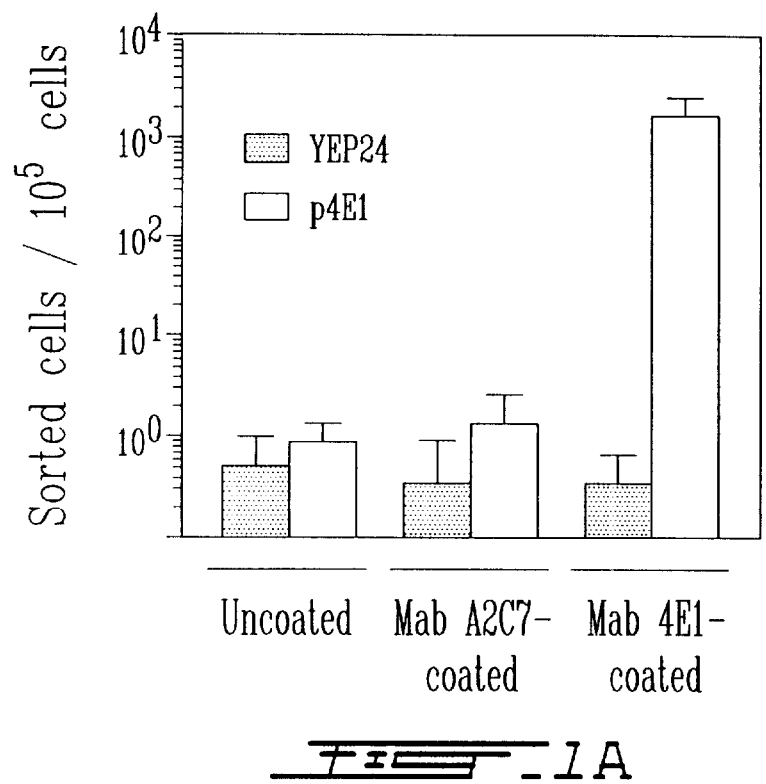
FIGS. 1A to 1C illustrate the sorting of *S. cerevisiae* transformants by uncoated, MAb A2C7- and MAb 4E1-coated magnetic beads.

In accordance with the present invention, there is provided an IgG MAb which strongly reacts with the terminal third of the growing filaments, but not with the parent blastospore, in *C. albicans* mycelial cultures. In immunoblots, the MAb 4E1 detected two species of 117 and 104 kDa from DTT-extracts prepared from the mycelial cells but not from yeast cells suggesting that the 4E1 antigen defines a true type I antigen.

To further characterize this surface antigen and also to confirm its differential expression in yeast versus hyphae, the corresponding gene was cloned. The inventors of the present invention reasoned that functional surface expression of this major mycelial antigen in the yeast *S. cerevisiae* might provide a simple and rapid approach to clone the corresponding gene. Using magnetic beads coated with MAb 4E1, *S. cerevisiae* transformants expressing a Candida genomic library were immunocaptured and Candida Surface Antigen 1 (CSA1) gene was cloned.

Experimental procedures
Strains and media

*Candida albicans* ATCC 32354 was used for the production of monoclonal antibodies and throughout this study. Yeast cells were cultured in Iscove's modified Dulbecco medium at 25° C. and mycelium formation was induced at 37° C., as described before. Disruption of CSA1 was performed in the *C. albicans* strain CAI4 (Fonzi, W. A., and Irwin, M. Y., *Genetics* 134: 717–728, 1993). The *S. cerevisiae* strain used was W303-1b (Thomas, B. J., and Rothstein, R., *Cell* 56: 619–630, 1989) (MATα ade2-1 can1-100 his3-11,15 leu2-3,112 trp1-1 ura3-1) which was grown at 30° C. in either YPD or SC-ura broth as described (Kaiser, C., et al., *Laboratory Course Manual for Methods in Yeast Genetics,* Cold Spring Harbor Laboratory, New York: Cold Spring Harbor Laboratory Press, 1994) for untransformed or transformed yeast, respectively. The *E. coli* strain used for plasmid purification and subcloning experiments was MC1061 and was cultured in 2×YT medium supplemented with 1% glucose and 50 µg/mL ampicillin.

DNA manipulations and transformations

All DNA manipulations were carried out according to standard procedures. All restriction enzymes and other DNA modifying enzymes were purchased from New England Biolabs (Mississauga, Ont.). Purification of total RNA was performed according to the procedure described by Kohrer and Domdey (Kohrer, K., and Domdey, H., *Methods Enzymol.* 194: 398–405, 1991). For the construction of the library and for Southern analysis, purification of genomic DNA from 40 mL yeast culture was carried out as described by Kaiser et al. (Kaiser, C., et al., *Laboratory Course Manual for Methods in Yeast Genetics,* Cold Spring Harbor Laboratory, New York: Cold Spring Harbor Laboratory Press, 1994). Standard procedures were used for Southern and Northern analyses. Nucleic acids were transferred onto nylon membranes in all cases (Hybond-N™; Amersham Life Science; Oakville, Ont.) and the radioactive probe was prepared with the Rediprime™ kit (Amersham Life Science) using [$^{32}$P]dCTP (ICN) according to the manufacturer's instructions. Automatic DNA sequencing reactions were performed by the dye terminator cycle protocol with dsDNA on a GeneAmp PCR system 9600 and a 373 DNA Sequencer (Applied Biosystems, Perkin Elmer; Mississauga, Ont.). Complete sequencing of CSA1 using universal primers was achieved by the construction of overlapping subclones in pTZ18R (Pharmacia Biotech; Baie d'Urfé, Que.). The CSA1 nucleotide sequence has been deposited in the GenBank database under the accession number AF080221.

Transformation of yeast using lithium acetate salt was performed according to the rapid procedure described by (Kaiser, C., et al., *Laboratory Course Manual for Methods in Yeast Genetics.* Cold Spring Harbor Laboratory, New York: Cold Spring Harbor Laboratory Press, 1994). The CaCl$_2$ protocol for transformation of *E. coli* was used for all subcloning experiments and recovery of the p4E1 plasmid from yeast whereas electroporation was used to construct the genomic library.

Construction of the *Candida albicans* genomic library

High molecular weight genomic DNA prepared as described above was partially digested with Sau3A I and size-selected on a discontinuous potassium acetate gradient (5–25%). Fractions containing DNA fragments >5 kg were pooled and ligated to the BamHI cut, dephosphorylated yeast 2µ plasmid YEP24. The ligation mixtures were then used to transform *E. coli* by electroporation. Approximately 15 000 total independent transformants were obtained, pooled into two aliquots of ~8 000 and 7 000 clones, and restriction digests performed on randomly selected plasmid DNA clones indicated that ~90% had an insert of an average size of 8 kb. Plasmid DNA prepared from pool I (~8 000 clones) was introduced into *S. cerevisiae* cells and the resulting transformants were selected onto SC-ura plates (~15). A total of ~30 000 colonies, were scraped from the selective solid medium, pooled into 10 mL of SC-ura and 1 mL aliquots were frozen at −80° C.

Screening of S. cerevisiae transformants with MAb-coated microspheres

Immunocapture of yeast transformants was performed with Sheep anti-mouse IgG-linked magnetic microspheres (Dynabeads™ M-280, Dynal; Lake Success, N.Y.) coated with MAb 4E1 and a particle concentrator (Dynal). Coating of the microspheres (1 mg) with MAb 4E1 (1 mL of hybridoma supernatant; ~50 µg/mL of IgG) was done by a 2 h incubation at room temperature in a rotary shaker. Coated-beads were then washed four times in phosphate-buffered saline supplemented with 0.1% bovine serum albumin (PBS-BSA) for 10 min each on a rotary shaker. As a negative control, the magnetic beads either uncoated or coated with MAb A2C7 (anti-enolase) were incubated under the same conditions. For immunoscreening, yeast transformants exponentially growing into SC-ura medium were harvested by low speed centrifugation and suspended into 1 mL of PBS-BSA at a final concentration of $1.5$ $O.D._{600}$/mL. Coated beads (100 µl; $6 \times 10^6$ beads) were then added and the suspension was rotated for 16 h at 4° C. At the end of the incubation, the microspheres were maintained on the wall of the tube by a lateral magnet and the supernatant was discarded. The beads were washed four times with PBS-BSA as described above. Free and cell-bound beads were finally recovered into 110 µL of PBS-BSA for plating onto SC-ura plates (100 µL) and microscopic examination (10 µL).

Magnetic bead sorting from homogenous cultures of S. cerevisiae carrying either YEP24 or p4E1 was performed essentially as described above with the following modifications. Exponentially growing cultures ($O.D._{600}$/mL between 1–1.5) were adjusted to a final cell density of $10^5$ cells/mL in PBS-BSA before the addition of the coated- (MAb 4E1) or uncoated beads ($10^6$/mL). The incubation was also done at room temperature for 2 h rather than overnight at 4° C. Finally, serial dilutions (10-fold) of the free- and cell-bound beads were plated onto selective SC-ura solid medium.

Competition experiments were conducted by first incubating the yeast transformants ($10^5$–$10^6$ cells) harvested from exponential cultures, and washed once with PBS-BSA, with either 1 mL of PBS-BSA or the MAb 4E1 supernatant for 1 h at room temperature before sorting with the coated microspheres.

Indirect immunofluorescence microscopy

Indirect immunofluorescence microscopy was carried out essentially as described by Pringle et al., (Pringle, J. R., et al., Methods Enzymol. 194: 565–602, 1991) using undiluted MAb 4E1 hybridoma supernatant as primary antibody and fluorescein-conjugated goat anti-mouse IgG antibodies (Bio/Can Scientific: Mississauga, Ont.) at 1/500 final dilution.

Disruption of CSA1

The 3.5 kb CAT:URA3::CAT cassette from plasmid pCUC (Fonzi, W. A., and Irwin, M. Y., Genetics 134: 717–728, 1993) was isolated by digestion with Bam HI and inserted at the Bam HI site of plasmid p4E1ΔS to create p4E1ΔS::CUC. The 4.6 kb fragment released from p4E1ΔS::CUC by digestion with Hpa I was used to transform C. albicans CAI4. Early logarithmic cells ($O.D._{600}$ 0.3) were transformed with approximately 5–10 µg of DNA. Cells were plated onto SC-ura medium. Approximately 3 transformants per µg of DNA were visible after 3 days of incubation at 30° C. Primary transformants were replated onto SC-ura medium containing uridine (50 µg/ml) and 5'-fluoorotic acid (FOA) (1 mg/ml) and FOA resistant colonies were subjected to further rounds of transformation. At each stage of this process, integration of the disrupting cassette at the CSA1 locus was confirmed by Southern analysis.

Results

Expression cloning of the C. albicans gene encoding the 4E1 antigen

In FIG. 1A, exponentially growing cultures of S. cerevisiae transformed with the indicated plasmids were sorted out with uncoated, MAb A2C7- and MAb 4E1-coated microspheres as described above. The results are expressed as the average number of colonies recovered per $10^5$ cells +/− SD from an experiment carried out in triplicate.

Experiments showed that S. cerevisiae cells transformed with the yeast multicopy plasmid YEP24 did not attach to either uncoated or MAb 4E1-coated magnetic beads (FIG. 1A). This indicated that there is no non-specific adherence of the cells to the beads and that the epitope recognized by MAb 4E1 is either not expressed or not exposed at the cell surface in this organism. S. cerevisiae was thus transformed with a C. albicans genomic library, and the pooled transformants were screened with the magnetic beads coated with MAb 4E1 during a 16 h incubation period at 4° C. Following extensive washes with PBS-BSA, the free and cell-bound microspheres were finally resuspended into the same buffer and spreaded onto selective agar plates (SC-ura). After an incubation of 3 days at 30° C. three colonies grew up on this medium. However, of the three plasmids recovered only one, designated p4E1, conferred the ability of freshly transformed S. cerevisiae cells to be sorted out by the coated beads. As assessed by colony formation on SC-ura plates, approximately 0.68% of the cells (676 +/− 111 per 100 000 cells) from exponentially growing cultures of the p4E1-transformant could be recovered with the coated beads (FIG. 1A). That this low level of sorting resulted from a specific interaction between the candidal antigen exposed at the surface of S. cerevisiae transformants and MAb 4E1 was first suggested by the dramatic reduction observed in the sorting efficiency (0.01%; 13 +/− 8 and 0.02%; 18 +/− 7 per 100 000 cells) when sorting was performed with uncoated and MAb A2C7-coated (anti-enolase) beads, respectively (FIG. 1A). This was confirmed by competition experiments where an excess of MAb 4E1 was incubated with exponentially growing p4E1-transformants prior to sorting with the coated microspheres (FIG. 1B).

Figure 1B:
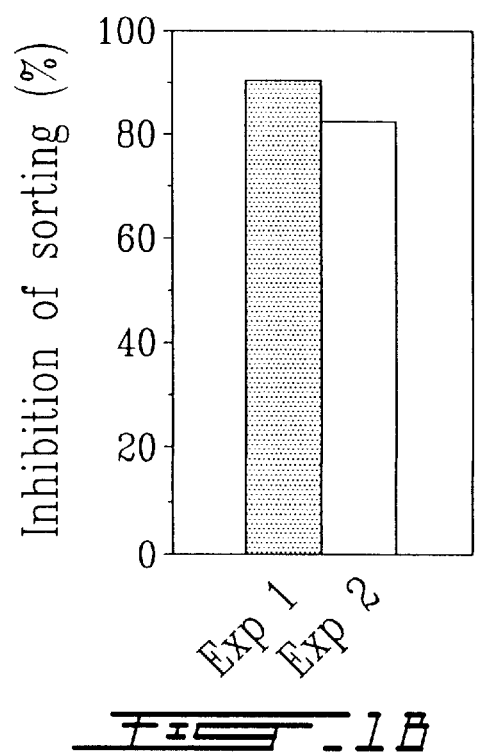

In FIG. 1B, either $10^5$ cells (Exp. 1) or $10^6$ cells (Exp. 2) from an exponentially growing culture of the S. cerevisiae transformed with p4E1 were first incubated with either MAb 4E1 or PBS-BSA prior to sorting with the MAb 4E1-coated microspheres. The results are expressed as the percentage of inhibition on the sorting resulting from a preincubation with MAb 4E1 as calculated from the number of colonies recovered with the coated beads.

Figure 1C:
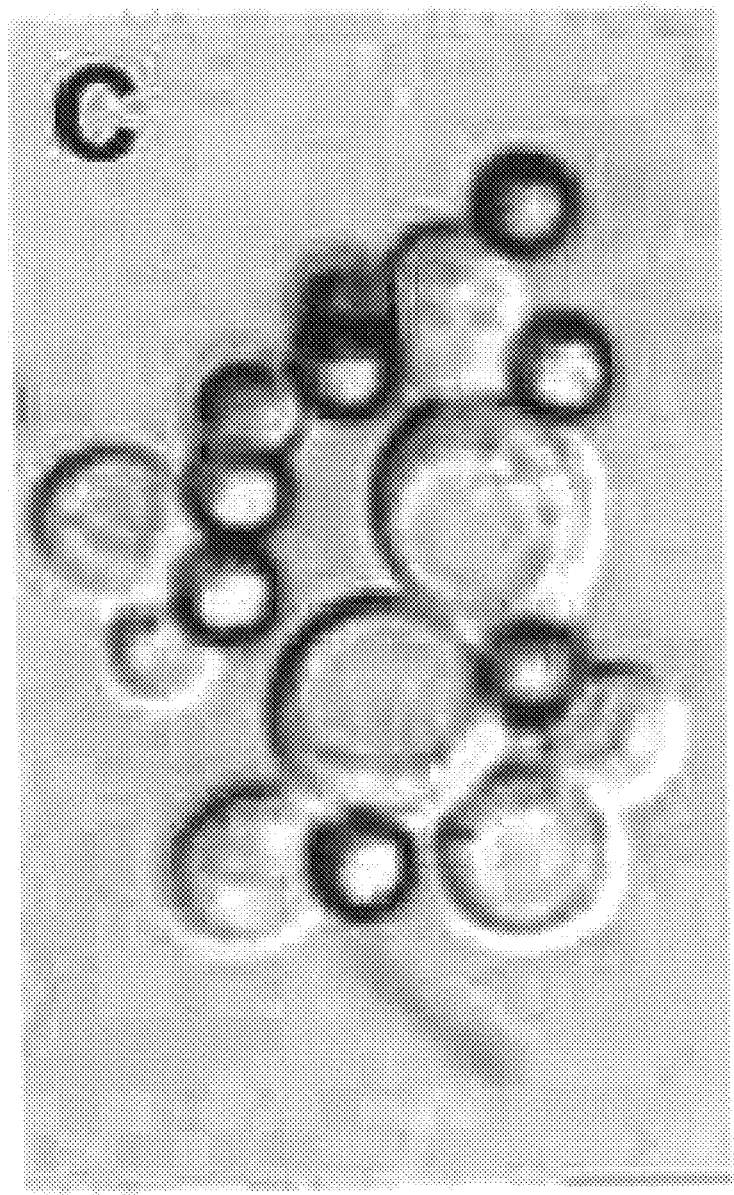

In the two parallel experiments (Exp. 1 and Exp. 2), competition with MAb 4E1 led to 90% and 82% inhibition in sorting, respectively. Therefore it is concluded that plasmid p4E1 carries the C. albicans gene coding for the 4E1 surface antigen. The low sorting efficiency of the yeast transformants also suggested a much reduced expression or surface exposure of this mycelial antigen in *S. cerevisiae* yeast cells compared to mycelial cultures of *C. albicans*. Microscopic examination of the MAb 4E1-sorted cells revealed that the microspheres were not randomly distributed over the cell surface but preferentially attached to the growing bud or at the mother-daughter neck junction (FIG. 1C). FIG. 1C illustrates representative differential interference contrast micrograph (100×) of the *S. cerevisiae* p4E1-transformant recovered with the MAb 4E1-coated magnetic beads.

Figure 2A:
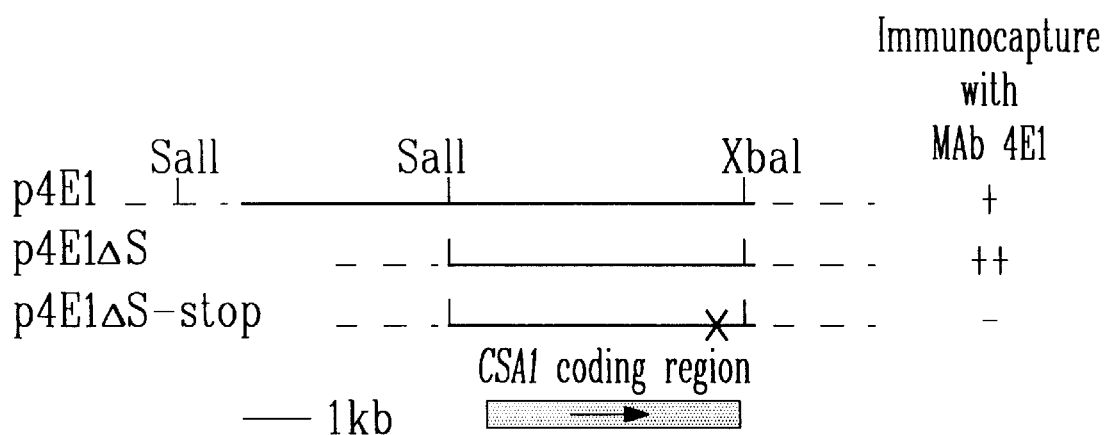
FIG. 2A illustrates a schematic representation of the genomic DNA fragments carried by the indicated plasmids and the ability of the corresponding yeast transformants to be sorted out by MAb 4E1-coated magnetic beads, (+) sorting and (−) no sorting.

The deduced amino acid sequence of CSA1 reveals the presence of repeated domains with sequence similarity to the *C. immitis* antigen 2 and *M. grisea* Pth11 protein Partial restriction mapping of plasmid p4E1 indicated that it carries a 7.4 kb genomic fragment (FIG. 2A). In FIG. 2A, the hatched box represents the CSA1 coding region and the arrow represents the direction of transcription. Subcloning experiments and immunocapture of the corresponding transformants showed that the gene encoding the 4E1 surface antigen (thereafter referred to as Candida Surface Antigen 1; CSA1) lies on the 4.2 kb Sal I-Xba I fragment (FIG. 2A). This genomic fragment was then entirely sequenced on both strands and found to contain a single, uninterrupted, open reading frame (ORF) of 3609 bp. In FIG. 2B, the predicted signal peptide (aa 1–17) and the hydrophobic stretch predicted to serve as GPI-anchoring determinant (aa 1184–1203) are in bold italics. The repeated hydrophilic sequences TSAP (SEQ ID NO:3) and P(A/S/V)ETS(E/Q) (SEQ ID NO:4) are underlined and twice underlined, respectively. The five CH domains are black boxed. The putative N-glycosylation sites located in the C-terminus of Csa1p are denoted by asterisks.

The deduced amino acid sequence of the ORF (1203 aa) revealed several important features (FIG. 2B). First, both the N- and C-termini contain a core of hydrophobic residues which may function as a signal sequence and a GPI-anchoring determinant, respectively. Anchoring to membranes through a GPI moiety is a common feature of many cell wall-associated proteins in fungi, including *C. albicans* and *S. cerevisiae*. That this putative GPI-anchoring determinant is important for the correct assembly of the 4E1 antigen into the cell wall is suggested by the observation that yeast expressing a C-terminal 164-aa truncated version of the protein cannot be sorted by the coated microspheres (FIG. 2A). A striking feature of the protein is a 102 residues cysteine-rich hydrophobic domain (CH domain) that is repeated 5 times in the sequence. The sequence identity between each domain exceeds 95%, except for the central repeat (aa 403–504 in Csa1p) which diverges slightly from the other repeats (84% sequence identity, ~94% sequence similarity). These CH domains are interspersed by segments of variable length (60 to 89 aa) almost exclusively composed (89%) of the residues P, E, T, S, A and Q, with an overall net charge of −54. Within these acidic-proline rich domains at least two motifs, TSAP (SEQ ID NO:3) and P(A/S/V)ETSS (E/Q) (SEQ ID NO:4), can be distinguished. A copy of the TSAP motif is always found upstream (15–16 aa) of a CH domain whereas the longer motif is repeated several times within the segments separating the CH domains. Finally, the 333-aa domain located between the last CH domain and the putative GPI-anchoring determinant (aa 852–1184), is also enriched in the residues P, E, T, S, A and Q (66%) with a net negative charge of −13. This domain contains all the putative N-glycosylation sites (10).

A search for sequence similarity in the *S. cerevisiae* protein database revealed that there is no homologue of Csa1p in this organism. However, a significant similarity was noticed between the CH domains of Csa1p, the immunoreactive antigen 2 (Ag2) of *Coccidioides immitis* and the Pth11 protein of *Magnaporthe grisea* (FIG. 3). In FIG. 3, alignment was performed with the CLUSTALW software available on the ExPASy molecular biology WWW server of the Swiss Institute of Bioinformatics. The sequence of Ag 2 was taken from Dugger et al. (Dugger, K. O., et al., *Biochem. Biophys. Res. Commun.* 218: 485–489, 1996). *C. immitis* is an important fungal human pathogen whereas *M. grisea* is a plant fungal pathogen responsible for the infection of the rice blast. The *C. immitis* Ag2 is a 194-aa protein that is expressed in the mycelium- and spherule-phase cell walls (Dugger, K. O., et al., *Biochem. Biophys. Res. Commun.* 218: 485–489, 1996). Pth11p is a 628- aa protein that acts as an upstream component of pathogenicity signaling in *M. grisea*. Amino acids 19–88 of Ag2 and 34–104 of Pth11p show 35% and 29% sequence identity (56% and 50% sequence similarity), respectively, with a 66-aa motif internal to the Csa1p CH domains. Remarkably, all the cysteine residues, with an insertion of a single amino acid in Ag2 align with those found in the Csa1p CH domains. In addition to the similarity in the primary amino acid sequence, the content of hydrophobic residues within this motif is similar (~26%) in all three proteins.

Figure 4:
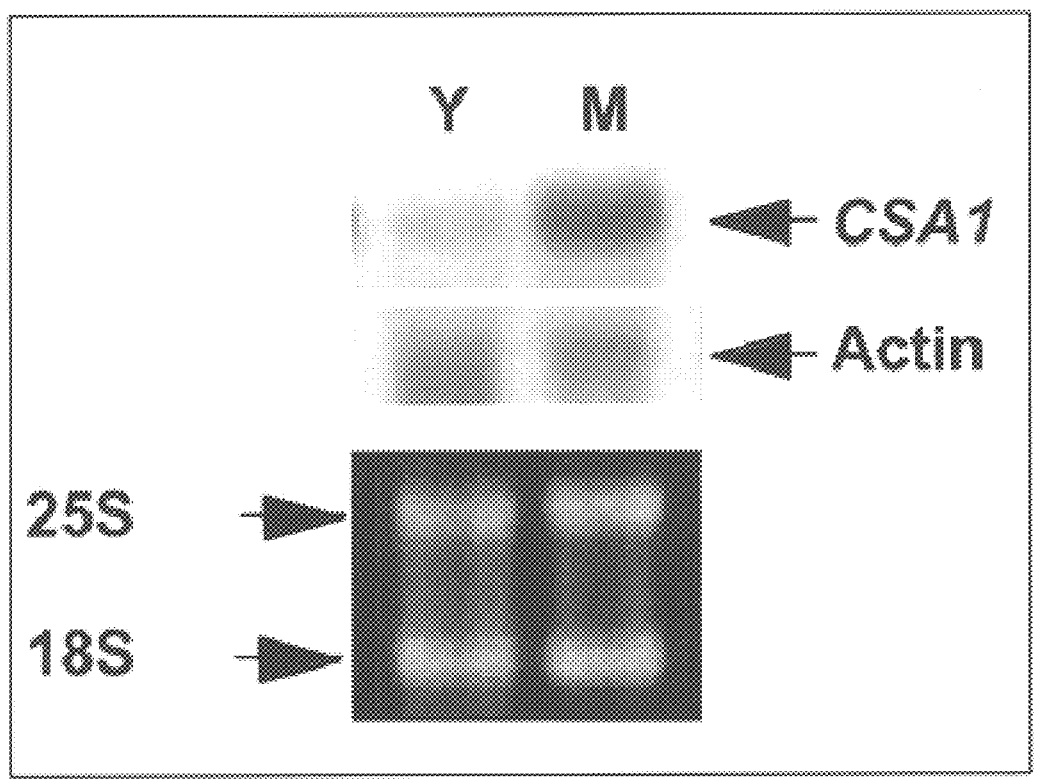
FIG. 4 illustrates a northern hybridization of total RNA extracted from the yeast and mycelial form of *C. albicans* with probes derived from CSA1 and the *S. cerevisiae* ACT1 gene.
Figure 5A:
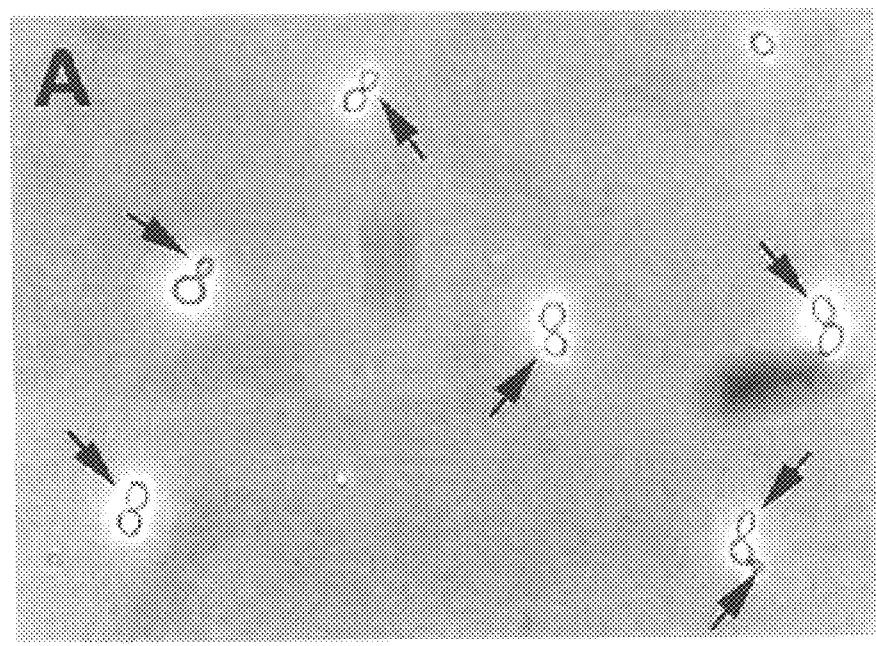
FIGS. 5A and 5B illustrate an indirect immunofluorescence microscopy of *C. albicans* yeast cells with MAb 4E1.
Figure 5B:
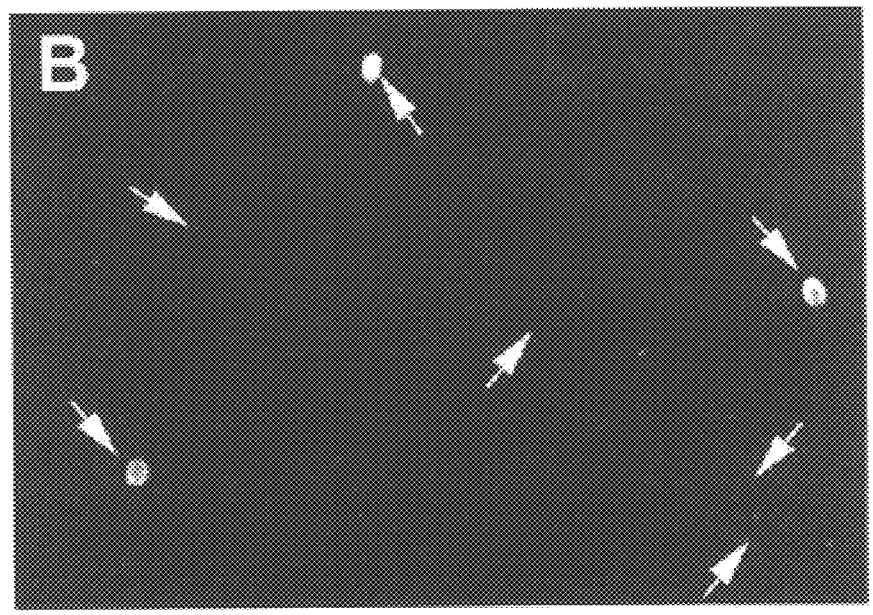

The 4E1 surface antigen can be detected in the growing buds of *C. albicans* yeast cells In the present invention, it was demonstrated above that the 4E1 surface antigen is exposed on the hyphal extensions in the mycelial form of *C. albicans* (Deslauriers, N., et al., *Microbiology* 142: 1239–1248, 1996). The antigen could not be detected either in the parent blastospore from mycelial cells or in the yeast form of *C. albicans*. Northern analysis confirmed the presence of an abundant CSA1 transcript (~4.0 kb) with total RNA extracted from *C. albicans* mycelial cultures (FIG. 4). In FIG. 4, Total RNA was prepared from *C. albicans* cultures growing in IMDM medium either at 25° C. (predominantly yeast cells; Y) or at 37° C. (mycelial cells; M). Identical amounts of total RNA (20 μg) were fractionated by agarose-formaldehyde gel and transferred onto nylon membrane. The RNA blot was then hybridized with the CSA1 3.9 kb Hpa I fragment and a probe derived from the *S. cerevisiae* ACT1 gene (actin). The top panel illustrates the autoradiogram of the Northern hybridization, whereas the bottom panel illustrates the ethidium Bromide staining of the agarose-formaldehyde gel. A low level of mRNA could however also be detected in the RNA sample prepared from *C. albicans* blastospores harvested during the early exponential growth phase. This, and the low level of expression of the surface antigen in *S. cerevisiae* yeast cells, therefore prompted the inventors to reexamine the presence of Csa1p by indirect immunofluorescence microscopy in *C. albicans* yeast cells (FIGS. 5A and 5B). FIG. 5A illustrates a bright field illumination micrograph (40×) of *C. albicans* yeast cells incubated with MAb 4E1 and the fluorescein-conjugated anti-mouse IgG secondary antibody, whereas FIG. 5B illustrates the epifluorescence micrograph of FIG. 5A. The arrows point to the cellular structures (FIG. 5A) reacting with the primary and secondary antibodies (FIG. 5B). As for the Northern analysis, the culture was grown to the early exponential phase to increase the proportion of budding yeast. Under these conditions MAb 4E1 reacted with a fraction of the cell population. As observed previously with the S. cerevisiae transformants, the antigen was detected predominantly, if not exclusively, in the growing buds. Control experiment where only the secondary fluorescein-conjugated antibody was added confirmed the specificity of the immunofluorescence profile. Hence, either a sub population of C. albicans yeast cells express Csa1p or the blastospores may transiently express the surface antigen during the budding process.

Figure 6A:
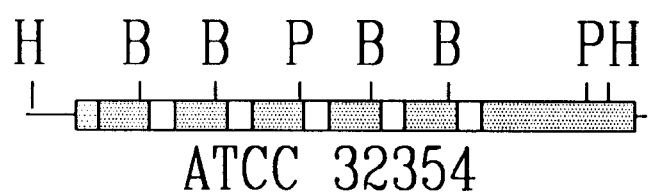
FIG. 6A illustrates a schematic representation of the CSA1 locus from strains ATCC 32354 and CAI4.
Figure 6A:
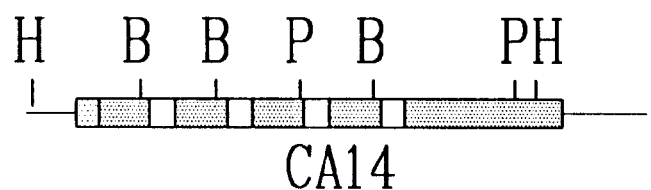
Figure 8B:
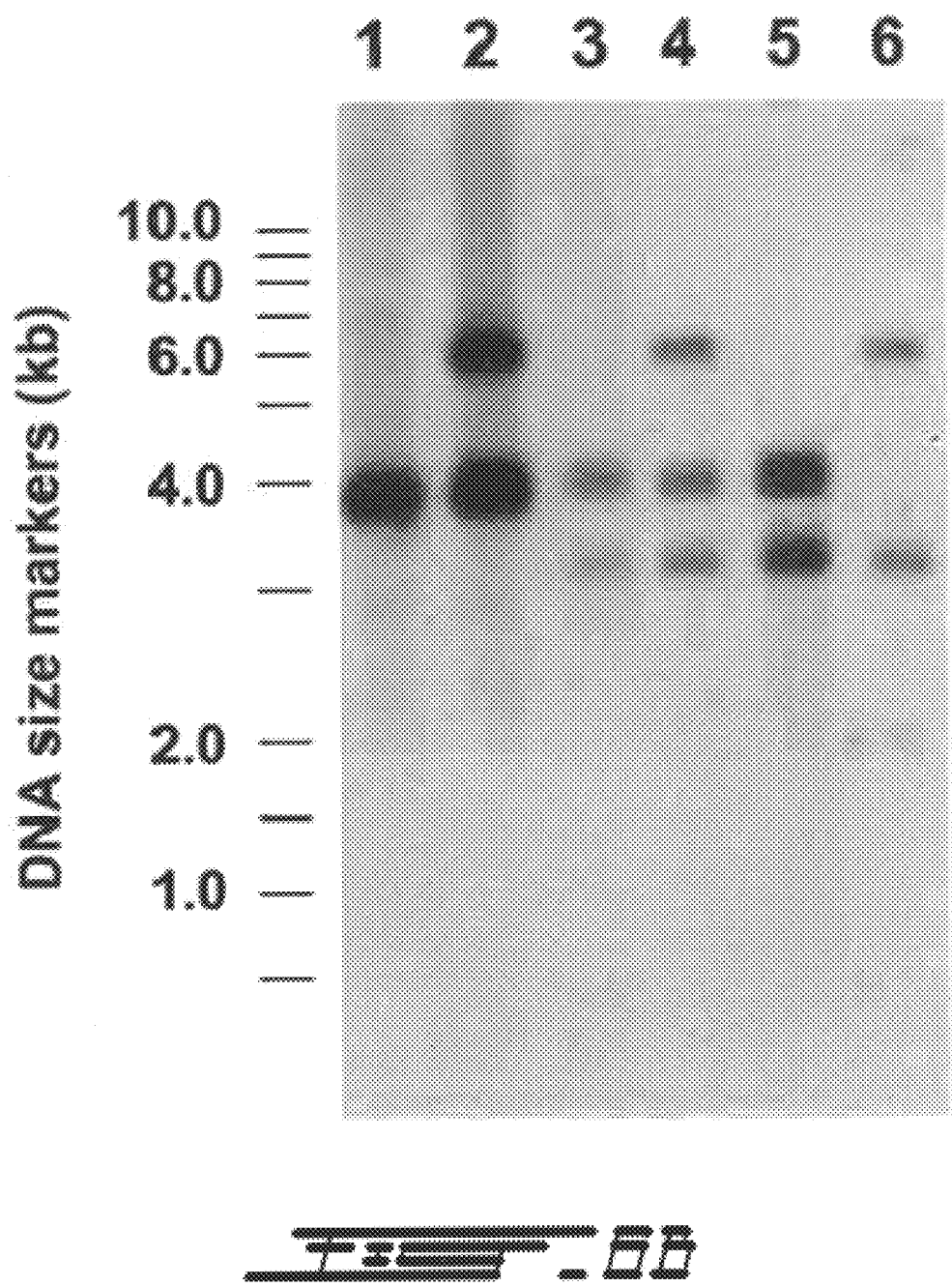

Disruption of CSA1 indicates that this gene is not essential for viability of either the yeast or mycelial form of C. albicans As a first step toward assessing the functional role of CSA1, a strain with disrupted alleles of this gene was constructed. As evidenced by Southern analysis (FIG. 6B), the parental strain (strain CAI4) used for the targeted disruption carries shorter alleles of CSA1 than that observed in the ATCC 32354 strain. The Hpa I fragment, which contains most of the CSA1 coding region and part of the 5' flanking sequence, is ~3.4 kb long in CAI4 compared to 3.9 kb in ATCC 32354. As predicted from the sequence of the gene five fragments, including a doublet of ~0.5 kb, should light up when the genomic DNA digested with Bam HI is probed with the Hpa I fragment (FIG. 6A). In FIG. 6A, grey and black boxes correspond respectively to the N- and C-terminal sequences of the CSA1 coding region. The hatched and open boxes represent the repeated CH domains the hydrophilic sequences, respectively. The relevant restriction sites are shown: B; Bam HI, H; Hpa I, P; Pst I. In FIG. 6B, the genomic DNA (10 µg) prepared from strains ATCC 32354 (A) and CAI4 (C) was digested with the indicated restriction enzymes, fractionated on agarose gel, transferred onto nylon membranes and probed with the CSA1 3.9 kb HpaI-fragment. The DNA size markers (1 kb ladder; Gibco-BRL) are indicated on the left. Fragments of identical sizes were observed in genomic DNA prepared from both strains. However, the signal intensity ratio of the 0.5 kb over the 1.0 kb fragment was significantly reduced for strain CAI4 compared to ATCC 32354. This strongly suggests that the alleles of CSA1 from CAI4 are missing one of the two 0.5 kb Bam HI fragments. To confirm this and to locate more precisely the deletion site, genomic DNA was digested with Pst I and again probed with the Hpa I fragment. In contrast to the ~1.8 kb predicted from the sequence, this revealed that the internal Pst I fragment of CSA1 is ~1.3 kb in size in strain CAI4. Collectively therefore, these results indicate that the alleles of CSA1 found in strain CAI4 lack the ~0.5 kb Bam HI fragment located toward the 3' end of the gene in strain ATCC 32354. Based on the nucleotide sequence, deletion of this Bam HI fragment predicts a protein composed of four instead of five CH domains.

Figure 7A:
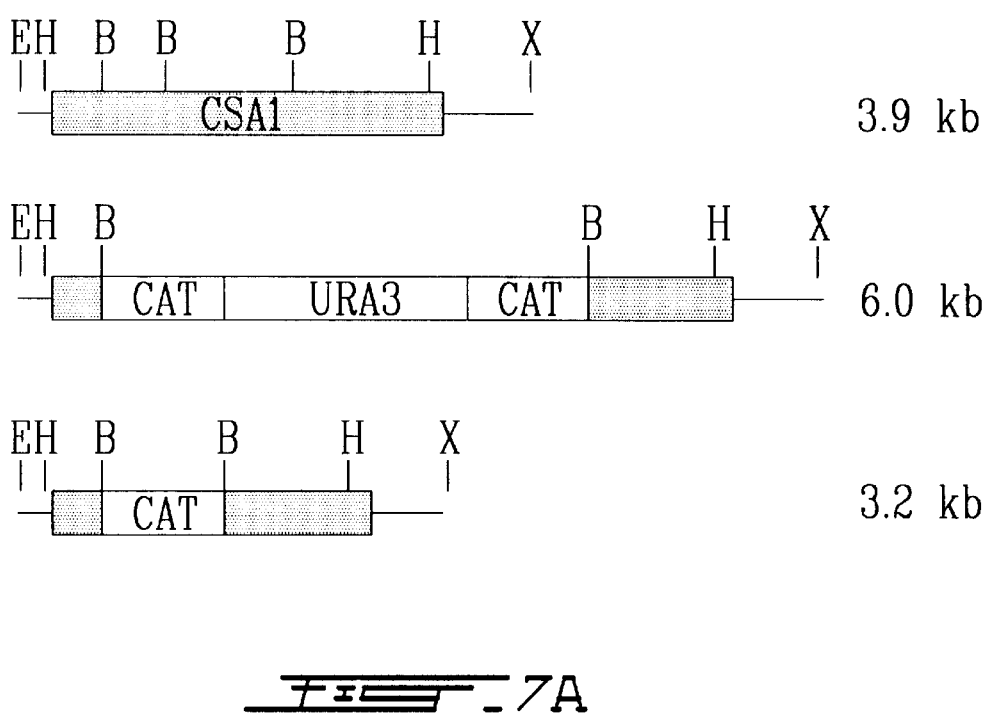
FIG. 7A illustrates a schematic representation of the wild type, CAT::URA::CAT- and CAT-disrupted alleles of CSA1 from strain CAI4.

The Ura-blaster technique was used to disrupt the CSA1 gene. The coding region of CSA1 internal to the Bam HI sites was replaced by the disrupting cassette composed of the CAT and URA3 sequences (FIG. 7A). The DNA was then restricted with Hpa I and the linear DNA fragment was used to transform strain CAI4. Integration of the disrupting cassette at the CSA1 locus was monitored, after each round of transformation, by Southern analysis of the genomic DNA prepared from the Ura+ transformants and digested with Eco RV and Xba I (FIG. 7B). In FIG. 7A, the grey boxes correspond to the CSA1 coding region. The size of the corresponding Eco RV-Xba I fragment is indicated on the right. The relevant restriction sites are shown: B; Bam HI, E; Eco RV, H; Hpa I, X; Xba I. In FIG. 7B, lane 1 represents the genomic DNA (10 µg) prepared from the parental strain CAI4, lane 2 represents a first-round Ura3$^+$ transformant, lane 3 represents a first-round FOA-resistant segregant, lane 4 represents a second-round Ura3$^+$ transformant, lane 5 represents a second-round FOA-resistant segregant, and lane 6 represents a third-round Ura3$^+$ transformant digested with Eco RV and Xba I. The resulting Southern blot was probed with the CSA1 Hpa I-Bam HI fragments. The DNA size markers (1 kb ladder; Gibco-BRL) are indicated on the left.

Following the second round of transformation, three bands of 6.0 kb, 3.9 kb and 3.2 kb corresponding to csa1::CAT-URA3-CAT, CSA1 and csa1::CAT respectively, were revealed by Southern analysis (FIG. 7B, lane 4). Hence, strain CAI4 is triploid at the CSA1 locus and a third round of transformation was required to get a strain lacking all functional alleles of this gene (FIG. 7B, lane 6).

The construction and selection of the csa1 mutants was carried out with the yeast form of C. albicans CAI4. Since Csa1p is weakly expressed in that form the viability of the knockout strain was therefore anticipated. However, all the mutant strains (single, double and triple deletions) showed the same viability when grown under conditions that elicit the transition from the yeast to the mycelial form (FIGS. 8A to 8F). Furthermore, the number and size of the hyphal extensions were similar in all three cultures. Hence, CSA1 is not essential for cell growth in either morphological phases and its absence does not preclude the emergence and elongation of the hyphal structures. Indirect immunofluorescence microscopy performed on the mycelial cells with MAb 4E1 indicated that the relative abundance of the surface antigen was subjected to a gene dosage effect (FIGS. 8A to 8F compare the relative fluorescence intensity between the single and double mutant). Most importantly, the antigen could not be detected in the triple mutant indicating that Csa1p is the only C. albicans surface antigen containing the 4E1 epitope. Differential interference contrast (FIGS. 8A to 8C) and epifluorescence (FIGS. 8D to 8F) micrograph (40×) of the single (FIGS. 8A and 8D), double (FIGS. 8B and 8E) and triple (FIGS. 8C and 8F csa1Δ deletant constructed in strain CAI4 are illustrated. The mycelial form was induced as described in FIG. 4 and the indirect immunofluorescence with MAb 4E1 was performed as in FIGS. 5A and 5B.

Discussion

The composition of the Candida albicans cell wall has been thoroughly studied and antigenic variations in cell wall mannoproteins as a function of dimorphism were investigated with polyclonal and monoclonal antibodies. These antibodies were most frequently directed toward carbohydrates carried by the cell wall proteins. In the present invention MAbs directed against C. albicans cell wall proteins have been produced and it is showed that MAb 4E1 recognizes proteinaceous antigens on the surface of mycelial cells. In the present invention, the inventors have cloned the corresponding gene as a first step toward understanding the role of this mycelial cell wall protein.

A number of expression cloning systems have been developed to isolate cDNA clones corresponding to cell surface molecules, and immunological screening by antibody capture after panning, FACS, or magnetic bead sorting was successfully used in mammalian cells. Here an adaptation of this approach for isolating $C.$ $albicans$ genes encoding cell surface molecules has been described. From ~$1.5 \times 10^7$ yeast cells derived from $8 \times 10^3$ independent transformants, three were sorted out by the MAb 4E1-coated magnetic beads and one carried the $C.$ $albicans$ gene CSA1 (p4E1 transformant) illustrating the exquisite selectivity of the technique. Since expression or surface exposure of this antigen appears to be restricted to a particular phase of the cell cycle and at a low level in budding yeast (see below), the method is also very sensitive. Immunocapture of $S.$ $cerevisiae$ transformants thus offers an attractive alternative for the identification of $C.$ $albicans$ genes encoding surface antigens. In both $C.$ $albicans$ and $S.$ $cerevisiae$ yeast cells the low level of expression of Csa1p was not randomly distributed over the cell surface, but localized predominantly in the growing buds. The strong induction of the CSA1 transcript observed upon transition from the yeast to the mycelial form and the absence of Csa1p from the parent blastospore suggest that the distribution of the antigen may be restricted to sites of cell surface elongation.

The primary amino acid sequence of Csa1p reveals the presence of repeated, nearly identical, cysteine-rich hydrophobic domains that are separated by acidic proline-rich hydrophilic domains composed of two repetitive units: TSAP and P(S/A/V)ETSS(E/Q). Interestingly, the number of repeats within CSA1 was found to be different from strains CAI4 and ATCC 32354 (FIG. 7A), as well as from various laboratory strains and clinical isolates. Tandem repeats have been found in surface proteins from a variety of organisms, including the $C.$ $albicans$ Als1, Hwp1 and Hyr1 cell wall proteins, and are frequently involved in host cell attachment, evasion of phagocytosis, invasion of host cells or act as neutralization epitopes. The role of these repeats is currently unknown. However, the presence of domains with sequence similarity to the Csa1p CH domains in surface proteins from two distantly related fungi, $C.$ $immitis$ and $M.$ $grisea,$ suggests a common function.

Cell surface hydrophobicity (CSH) in $C.$ $albicans$ and $M.$ $grisea$ has been linked to a plethora of host interactions and fungal functions, and several surface proteins are thought to be involved in CSH in $C.$ $albicans$. Given the hydrophobic character of the CH domain and the preferential expression of Csa1p during the mycelial growth phase, its potential function may be to increase the overall hydrophobicity of the fungal cell wall associated with the transition from the yeast to the mycelial form. In support of this hypothesis the CH domains of Csa1p, and the analogous domains found in Ag2 and Pth11p, present similitude to a class of small secreted fungal proteins (96–125 aa) called hydrophobins. Hydrophobins from different species have now been identified. They present a weak sequence identity (4%) but they all possess 8 cysteine residues dispersed throughout a sequence rich in proline and hydrophobic amino acids. Despite their weak sequence identity they appear to be functionally interchangeable (Kershaw, M. J., et al., $EMBO$ $L.$ 17: 3838–3849, 1998). In response to environmental stimuli, these molecules self-assemble into polymeric structures to form a coat that increases dramatically the hydrophobic character of the fungal cell walls.

Morphogenesis in $C.$ $albicans$ is more than a change in cell shape and entails the expression of physiological attributes linked to its performance as a successful commensal and opportunistic pathogen. Until now molecular genetic approaches have identified a few genes encoding hyphae-specific surface proteins that may contribute to differences in cell wall structure and functions. In the present invention, it is now reported that $C.$ $albicans$ Csa1p is a non-essential protein differentially expressed in blastospores and mycelia. Its accessibility to external ligands, its dynamic expression and hydrophobic character together with its sequence similarity to domains found in the immunogenic Ag2 protein ($C.$ $immitis$) and Pth11p ($M.$ $grisea$) suggest that this protein may be involved in surface interactions with its changing molecular and cellular environment.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated nucleic acid sequence as set forth in SEQ. ID NO:1.

2. A diagnostic kit for detecting *Candida albicans* infection in a sample of a nucleic acid sequence of a patient, said kit comprising an isolated nucleic acid as set forth in SEQ ID NO:1.

* * * * *

SEQUENCE LISTING

```
<160> NUMBER OF SEQ ID NOS: 4

<210> SEQ ID NO 1
<211> LENGTH: 4291
<212> TYPE: DNA
<213> ORGANISM: Candida albicans
<220> FEATURE:
<221> NAME/KEY: gene
<222> LOCATION: (0)...(0)
```

-continued

```
<400> SEQUENCE: 1
gtcgacacaa taagctaaat agagtgcagt aagatgtgat tgtcatctttt agtagatgct      60 cctataggta attgtataag gttattgcgg agttaacgct ggtattgggt ttcgcttggt     120
agtttctagt attggcacta aaattttttt tttcttgttt gtcgcacaca cagttgattg     180
gctagaatta aagctcaact ttgcacaatt taaaaacaat gcattaggcg atttatcgcg     240
taaattaatt accacaacaa agaacaactt attttccgat tgtccaatca atgtcatagg     300
tgttctcggg tttgttacaa tgtctggaaa tatcgaaaac ttacgataat ttaaatgttg     360
gtttgtggat tttagaaggg ataatacaat gattggatag cactaagtcc cgtatagttc     420
gacaacggtt tatttgggtt actacttata gagccctggt ccccagaatt tgaaaatgta     480
gttggttgtg aaacactcag ggatatactc aacaatgctt ccatccattg ttatttcaat     540
cgttttagca tcctttgtga gtgcagaatc atctattaca gaagcaccaa caacaaccgc     600
tgaagataat ccatatacta tctacccaag tgttgccaag actgcttcta tcaatggttt     660
tgctgacaga atttatgatc aattgccaga gtgtgccaag ccatgtatgt tccaaaacac     720
tggtgtgacc ccatgtccat actgggatac tgggtgtttg tgtattatgc caacatttgc     780
tggtgccatt ggttcttgta ttgctgagaa gtgtaaaggc caagacgttg tttctgctac     840
aagtttggga acttccattt gttccgttgc tggtgtgtgg gatccatact ggatggtgcc     900
tgcaaatgtc cagagcagtt taagtgctgc tgccactgct gttgcatcgt cttctgaaca     960
accagttgaa acatcttctg aaccagctgg atcttctcag tctgttgaat cttctcaacc    1020
tgctgaaacc tcatcatctg aacctgctga gacttcatca tctgaacctg ctgagacttc    1080
atcggaaaca tcatccgaac aacctgcttc atctgaacct gctgaaactt catcagaaga    1140
atcttctaca atcacttcag ccccatcaac tcctgaagat aacccataca ccatctaccc    1200
aagtgttgcc aagactgctt ctatcaatgg ttttgctgac agaatctacg accaattgcc    1260
agagtgtgcc aagccatgta tgttccaaaa cactggtgtg accccatgtc catactggga    1320
tactgggtgc ttgtgtatta tgccaacatt tgctggtgcc attgggtctt gtattgctga    1380
gaagtgtaaa ggccaagacg ttgttgctgc tacaagtttg ggaacttcca tttgttccgt    1440
tgctggtgtg tgggatccat actggatggt gcctgcaaat gtccagagca gtttaagtgc    1500
tgctgccact gctgttccat catcctccga acaatcagtt gaaacatctt ctgaatcagc    1560
tgaatcttct cagtctgttg aatcttctca acctgctgaa acctcatctg aacaaccatc    1620
tgagacttca tctgaaactt cttcccaaca actttcaagt atcacttcag caccagactc    1680
ctccgctaca agcagctcct caaccacatc tactttttatt agaactgctt ccattaatgg    1740
ttttgctgat aaactttacg accaattacc agaatgtgct aaaccatgta tgttccaaaa    1800
tactggcata acaccatgtc catactggga tgccggttgt ttatgtgtca tgccacaatt    1860
tgcaggtgct attggttcat gtgttgccga tagttgtaaa ggtcaagata ttgtttctgt    1920
caccagcttg ggtacttctg tttgttctgt tgccggtgtt aatgcacctt attggatgct    1980
tccagctagt gttaaaagta gcttaagtgt tgctgctact gcagtaccaa cctccgacag    2040
tgcatctgaa actgcttccc aagaaccatc tgaaacttca tctgaacagc atcagaaac    2100 tgcttcacaa caacctgctg aaacttcatc agaagaatct tctacaatca cttcagcccc    2160
atcaactcct gaagataacc catacaccat ctacccaagt gttgccaaga ctgcttctat    2220
caatggtttt gctgacagaa tctacgacca attgccagag tgtgccaagc catgtatgtt    2280
ccaaaacact ggtgtgaccc catgtccata ctgggatact gggtgcttgt gtattatgcc    2340
```

```
aacatttgct ggtgccattg ggtcttgtat tgctgagaag tgtaaaggcc aagacgttgt    2400
ttctgctaca agtttgggaa cttccatttg ttccgtcgct ggtgtatggg atccatattg    2460
gatgattcca gctaatgcac aaagcagttt gaatgctgct gccactgctg ttgcatcatc    2520
ttctgaacaa ccagttgaaa catcttctga agctgctgaa tcttctcaaa atcctgctga    2580
atcttcttct caacaaccat ctgaaactgc ttctcaagaa ccatctgaaa cttcttccca    2640
agaaccatca gaaagctcat cagagcaacc tgctgagact tcatcagaag aatcttctac    2700
catcacttca gctccatcaa ctcctgaaga taatccatac accatctacc caagtgttgc    2760
caagactgct tctatcaatg gttttgctga cagaatttat gatcaattgc agagtgtgc     2820 caagccatgt atgttccaaa acactggtgt gaccccatgt ccatactggg atactgggtg    2880
cttgtgtatt atgccaacat tgctggtgc cattgggtct tgtattgctg agaaatgtaa     2940
aggacaagag gttgtttctg ttacaagttt gggtagctct atttgttccg ttgctggtgt    3000
atgggatcca tactggatgc ttccagctaa cgtgcaaagc agtttgaatg ccgctgccac    3060
tgctgttgca acttctgata gtgcatctga ggttgcttct gcttccgaat ccgcatctca    3120
agttccacaa gaaacttctg ctgcttcatc acaatcagcc aacaactcag ttgcttctgc    3180
tgctccatct aactcgtctg tttcagctgc tccatctagc aactcatctg gtgttccagc    3240
tgcgccatct aacaattcat ctggtgcttc agttgttcca tcacaatcag ccaacaattc    3300
atctgcttca gctgctccat ctaacaactc atctagtgct atttctggaa gtgttgcacc    3360
atcaagctac ggaaactcta ccattgcaca accatctact tctacaaaat ccgatgctgc    3420
atcaattact ggtccaatta ctacagacaa ggttataacc aatgagtctg gcattgtctt    3480
tacatctaca gtaatcatta cacatgtttc tgaatattgt gaccagactt ctgctgctgc    3540
tgttcaatca tcagcatgtg aagaacagtc aagtgctaaa tcagaacaag cttctgcttc    3600
atcagaacaa gttaaggtca ttactagtgt ggtttggtgt gagtcatcta ttcaatctat    3660
tgaatctgtc aaaacaagtg cagaagctgc tcataagact gaggttattg ctagttgtgc    3720
aagtgaatta agctctttga gttctgctaa atctgaagct atgaagactg tttctagttt    3780
agttgaagtt caaaaatctg cagttgccaa acaaacctcg ttggctgctg tacaatcatc    3840
tgctgcttct gtacaattaa gtgctgctca cgcccaaaag tcgtctgagg cagttgaagt    3900
tgcccaaact gctgttgctg aagcttctaa agctggtgat gaaatttcga ctgaaattgt    3960
taacatcacc aagacagttt cttctggtaa ggagactggt gtttcccaag ctactgttgc    4020
tgctaacaca cattcagttg ctattgctaa tatggcaaat accaagtttg ccagcacaat    4080
gtcgttgttg gtcgctagtt tcgtgtttgt tggtctcttt atttaagagg tataataagt    4140
tcttataatt ttcttgataa atttattttt tttctgtttt cggttactat atgtataaag    4200
ttttgttaat actataattt ttttgttagc ctcggtattt cttaaaatag ttgtaaattc    4260
acccaaatag gaagacagaa aaaagtctag a                                    4291
```

<210> SEQ ID NO 2
<211> LENGTH: 1203
<212> TYPE: PRT
<213> ORGANISM: Candida albicans
<220> FEATURE:
<221> NAME/KEY: PEPTIDE
<222> LOCATION: (0)...(0)

<400> SEQUENCE: 2

Met Leu Pro Ser Ile Val Ile Ser Ile Val Leu Ala Ser Phe Val Ser

```
              1               5                   10                  15
    Ala Glu Ser Ser Ile Thr Glu Ala Pro Thr Thr Thr Ala Glu Asp Asn
                        20                  25                  30
    Pro Tyr Thr Ile Tyr Pro Ser Val Ala Lys Thr Ala Ser Ile Asn Gly
                    35                  40                  45
    Phe Ala Asp Arg Ile Tyr Asp Gln Leu Pro Glu Cys Ala Lys Pro Cys
        50                  55                  60
    Met Phe Gln Asn Thr Gly Val Thr Pro Cys Pro Tyr Trp Asp Thr Gly
    65                  70                  75                  80
    Cys Leu Cys Ile Met Pro Thr Phe Ala Gly Ala Ile Gly Ser Cys Ile
                        85                  90                  95
    Ala Glu Lys Cys Lys Gly Gln Asp Val Val Ser Ala Thr Ser Leu Gly
                    100                 105                 110
    Thr Ser Ile Cys Ser Val Ala Gly Val Trp Asp Pro Tyr Trp Met Val
                    115                 120                 125
    Pro Ala Asn Val Gln Ser Ser Leu Ser Ala Ala Thr Ala Val Ala
        130                 135                 140
    Ser Ser Ser Glu Gln Pro Val Glu Thr Ser Ser Glu Pro Ala Gly Ser
    145                 150                 155                 160
    Ser Gln Ser Val Glu Ser Ser Gln Pro Ala Glu Thr Ser Ser Ser Glu
                    165                 170                 175
    Pro Ala Glu Thr Ser Ser Ser Glu Pro Ala Glu Thr Ser Ser Glu Thr
                    180                 185                 190
    Ser Ser Glu Gln Pro Ala Ser Ser Glu Pro Ala Glu Thr Ser Ser Glu
                    195                 200                 205
    Glu Ser Ser Thr Ile Thr Ser Ala Pro Ser Thr Pro Glu Asp Asn Pro
        210                 215                 220
    Tyr Thr Ile Tyr Pro Ser Val Ala Lys Thr Ala Ser Ile Asn Gly Phe
    225                 230                 235                 240
    Ala Asp Arg Ile Tyr Asp Gln Leu Pro Glu Cys Ala Lys Pro Cys Met
                    245                 250                 255
    Phe Gln Asn Thr Gly Val Thr Pro Cys Pro Tyr Trp Asp Thr Gly Cys
                    260                 265                 270
    Leu Cys Ile Met Pro Thr Phe Ala Gly Ala Ile Gly Ser Cys Ile Ala
        275                 280                 285
    Glu Lys Cys Lys Gly Gln Asp Val Val Ala Ala Thr Ser Leu Gly Thr
    290                 295                 300
    Ser Ile Cys Ser Val Ala Gly Val Trp Asp Pro Tyr Trp Met Val Pro
    305                 310                 315                 320
    Ala Asn Val Gln Ser Ser Leu Ser Ala Ala Thr Ala Val Pro Ser
                    325                 330                 335
    Ser Ser Glu Gln Ser Val Glu Thr Ser Ser Glu Ser Ala Glu Ser Ser
                    340                 345                 350
    Gln Ser Val Glu Ser Ser Gln Pro Ala Glu Thr Ser Glu Gln Pro
                    355                 360                 365
    Ser Glu Thr Ser Ser Glu Thr Ser Ser Gln Gln Leu Ser Ser Ile Thr
        370                 375                 380
    Ser Ala Pro Asp Ser Ser Ala Thr Ser Ser Ser Thr Thr Ser Thr
    385                 390                 395                 400
    Phe Ile Arg Thr Ala Ser Ile Asn Gly Phe Ala Asp Lys Leu Tyr Asp
                    405                 410                 415
    Gln Leu Pro Glu Cys Ala Lys Pro Cys Met Phe Gln Asn Thr Gly Ile
                    420                 425                 430
```

-continued

```
Thr Pro Cys Pro Tyr Trp Asp Ala Gly Cys Leu Cys Val Met Pro Gln
        435                 440                 445
Phe Ala Gly Ala Ile Gly Ser Cys Val Ala Asp Ser Cys Lys Gly Gln
        450                 455                 460
Asp Ile Val Ser Val Thr Ser Leu Gly Thr Ser Val Cys Ser Val Ala
465                 470                 475                 480
Gly Val Asn Ala Pro Tyr Trp Met Leu Pro Ala Ser Val Lys Ser Ser
                    485                 490                 495
Leu Ser Val Ala Ala Thr Ala Val Pro Thr Ser Asp Ser Ala Ser Glu
            500                 505                 510
Thr Ala Ser Gln Glu Pro Ser Glu Thr Ser Ser Glu Gln Pro Ser Glu
            515                 520                 525
Thr Ala Ser Gln Gln Pro Ala Glu Thr Ser Ser Glu Glu Ser Ser Thr
        530                 535                 540
Ile Thr Ser Ala Pro Ser Thr Pro Glu Asp Asn Pro Tyr Thr Ile Tyr
545                 550                 555                 560
Pro Ser Val Ala Lys Thr Ala Ser Ile Asn Gly Phe Ala Asp Arg Ile
                565                 570                 575
Tyr Asp Gln Leu Pro Glu Cys Ala Lys Pro Cys Met Phe Gln Asn Thr
            580                 585                 590
Gly Val Thr Pro Cys Pro Tyr Trp Asp Thr Gly Cys Leu Cys Ile Met
            595                 600                 605
Pro Thr Phe Ala Gly Ala Ile Gly Ser Cys Ile Ala Glu Lys Cys Lys
        610                 615                 620
Gly Gln Asp Val Val Ser Ala Thr Ser Leu Gly Thr Ser Ile Cys Ser
625                 630                 635                 640
Val Ala Gly Val Trp Asp Pro Tyr Trp Met Ile Pro Ala Asn Ala Gln
                645                 650                 655
Ser Ser Leu Asn Ala Ala Thr Ala Val Ala Ser Ser Ser Glu Gln
            660                 665                 670
Pro Val Glu Thr Ser Ser Glu Ala Ala Glu Ser Ser Gln Asn Pro Ala
            675                 680                 685
Glu Ser Ser Gln Gln Pro Ser Glu Thr Ala Ser Gln Glu Pro Ser
        690                 695                 700
Glu Thr Ser Ser Gln Glu Pro Ser Glu Ser Ser Glu Gln Pro Ala
705                 710                 715                 720
Glu Thr Ser Ser Glu Glu Ser Ser Thr Ile Thr Ser Ala Pro Ser Thr
                725                 730                 735
Pro Glu Asp Asn Pro Tyr Thr Ile Tyr Pro Ser Val Ala Lys Thr Ala
            740                 745                 750
Ser Ile Asn Gly Phe Ala Asp Arg Ile Tyr Asp Gln Leu Pro Glu Cys
            755                 760                 765
Ala Lys Pro Cys Met Phe Gln Asn Thr Gly Val Thr Pro Cys Pro Tyr
        770                 775                 780
Trp Asp Thr Gly Cys Leu Cys Ile Met Pro Thr Phe Ala Gly Ala Ile
785                 790                 795                 800
Gly Ser Cys Ile Ala Glu Lys Cys Lys Gly Gln Glu Val Val Ser Val
                805                 810                 815
Thr Ser Leu Gly Ser Ser Ile Cys Ser Val Ala Gly Val Trp Asp Pro
            820                 825                 830
Tyr Trp Met Leu Pro Ala Asn Val Gln Ser Ser Leu Asn Ala Ala Ala
        835                 840                 845
```

```
            Thr Ala Val Ala Thr Ser Asp Ser Ala Ser Glu Val Ala Ser Ala Ser
                850                 855                 860

Glu Ser Ala Ser Gln Val Pro Gln Glu Thr Ser Ala Ala Ser Ser Gln
            865                 870                 875                 880

Ser Ala Asn Asn Ser Val Ala Ser Ala Pro Ser Asn Ser Ser Val
                            885                 890                 895

Ser Ala Ala Pro Ser Ser Asn Ser Ser Gly Val Pro Ala Ala Pro Ser
                        900                 905                 910

Asn Asn Ser Ser Gly Ala Ser Val Val Pro Ser Gln Ser Ala Asn Asn
                            915                 920                 925

Ser Ser Ala Ser Ala Ala Pro Ser Asn Asn Ser Ser Ser Ala Ile Ser
                        930                 935                 940

Gly Ser Val Ala Pro Ser Ser Tyr Gly Asn Ser Thr Ile Ala Gln Pro
            945                 950                 955                 960

Ser Thr Ser Thr Lys Ser Asp Ala Ala Ser Ile Thr Gly Pro Ile Thr
                            965                 970                 975

Thr Asp Lys Val Ile Thr Asn Glu Ser Gly Ile Val Phe Thr Ser Thr
                        980                 985                 990

Val Ile Ile Thr His Val Ser Glu Tyr Cys Asp Gln Thr Ser Ala Ala
                        995                 1000                 1005

Ala Val Gln Ser Ser Ala Cys Glu Glu Gln Ser Ser Ala Lys Ser Glu
                        1010                1015                 1020

Gln Ala Ser Ala Ser Ser Glu Gln Val Lys Val Ile Thr Ser Val Val
            1025                1030                1035                 1040

Trp Cys Glu Ser Ser Ile Gln Ser Ile Glu Ser Val Lys Thr Ser Ala
                            1045                1050                 1055

Glu Ala Ala His Lys Thr Glu Val Ile Ala Ser Cys Ala Ser Glu Leu
                        1060                1065                 1070

Ser Ser Leu Ser Ser Ala Lys Ser Glu Ala Met Lys Thr Val Ser Ser
                        1075                1080                 1085

Leu Val Glu Val Gln Lys Ser Ala Val Ala Lys Gln Thr Ser Leu Ala
                        1090                1095                1100

Ala Val Gln Ser Ser Ala Ala Ser Val Gln Leu Ser Ala Ala His Ala
            1105                1110                1115                 1120

Gln Lys Ser Ser Glu Ala Val Glu Val Ala Gln Thr Ala Val Ala Glu
                            1125                1130                 1135

Ala Ser Lys Ala Gly Asp Glu Ile Ser Thr Glu Ile Val Asn Ile Thr
                        1140                1145                1150

Lys Thr Val Ser Ser Gly Lys Glu Thr Gly Val Ser Gln Ala Thr Val
                        1155                1160                 1165

Ala Ala Asn Thr His Ser Val Ala Ile Ala Asn Met Ala Asn Thr Lys
            1170                1175                1180

Phe Ala Ser Thr Met Ser Leu Leu Val Ala Ser Phe Val Phe Val Gly
            1185                1190                1195                1200

Leu Phe Ile

<210> SEQ ID NO 3
<211> LENGTH: 4
<212> TYPE: PRT
<213> ORGANISM: Candida albicans
<220> FEATURE:
<221> NAME/KEY: REPEAT
<222> LOCATION: (0)...(0)

<400> SEQUENCE: 3
```

```
Thr Ser Ala Pro
 1

<210> SEQ ID NO 4
<211> LENGTH: 6
<212> TYPE: PRT
<213> ORGANISM: Candida albicans
<220> FEATURE:
<221> NAME/KEY: REPEAT
<222> LOCATION: (0)...(0)
<223> OTHER INFORMATION: Xaa in position 2 can be Ala, Ser or Val
<223> OTHER INFORMATION: Xaa in position 6 can be Glu or Gln

<400> SEQUENCE: 4

Pro Xaa Glu Thr Ser Xaa
 1               5
```